United States Patent [19]
Kurtz et al.

[11] Patent Number: 5,501,680
[45] Date of Patent: Mar. 26, 1996

[54] BOUNDARY AND PROXIMITY SENSOR APPARATUS FOR A LASER

[75] Inventors: John L. Kurtz, Indiana; Marc D. Liang; Krishna Narayanan, both of Pittsburgh, all of Pa.

[73] Assignee: The University of Pittsburgh, Pittsburgh, Pa.

[21] Appl. No.: 821,404

[22] Filed: Jan. 15, 1992

[51] Int. Cl.⁶ .................................................. A61B 17/36
[52] U.S. Cl. ...................... 606/9; 606/10; 606/12
[58] Field of Search ............................. 606/4–6, 9–17; 607/88, 89

[56] References Cited

U.S. PATENT DOCUMENTS

| | | | |
|---|---|---|---|
| 4,316,467 | 2/1982 | Muckerheide | 606/12 |
| 4,641,650 | 2/1987 | Mok | 606/12 |
| 4,644,948 | 2/1987 | Lang et al. | 606/12 |
| 4,686,979 | 8/1987 | Gruen et al. | 606/15 X |
| 4,785,806 | 11/1988 | Deckelbaum | 606/15 X |
| 5,035,693 | 7/1991 | Kratzer et al. | 606/12 |
| 5,053,006 | 10/1991 | Watson | 604/52 |
| 5,057,102 | 10/1991 | Tomioka et al. | 606/12 X |
| 5,071,417 | 12/1991 | Sinofsky | 606/12 X |

*Primary Examiner*—Stephen C. Pellegrino
*Assistant Examiner*—M. Peffley
*Attorney, Agent, or Firm*—Reed Smith Shaw & McClay

[57] ABSTRACT

A laser operation and control system preferably comprising a laser adapted to be grasped by a user and freely passed over a treatment area, control circuitry for activating and deactivating the laser, at least one boundary sensor operable to transmit a signal to the control circuitry to deactivate the laser upon passage thereof beyond a boundary of the treatment area and to transmit a signal to the control circuitry to activate the laser upon passage thereof within the boundary, and at least one proximity sensor for transmitting a signal to the control circuitry to deactivate the laser should the proximity sensor fail to sense a substantially solid surface within a predetermined distance therefrom and for transmitting a signal to the control circuitry to activate the laser should the proximity sensor sense such a surface.

36 Claims, 4 Drawing Sheets

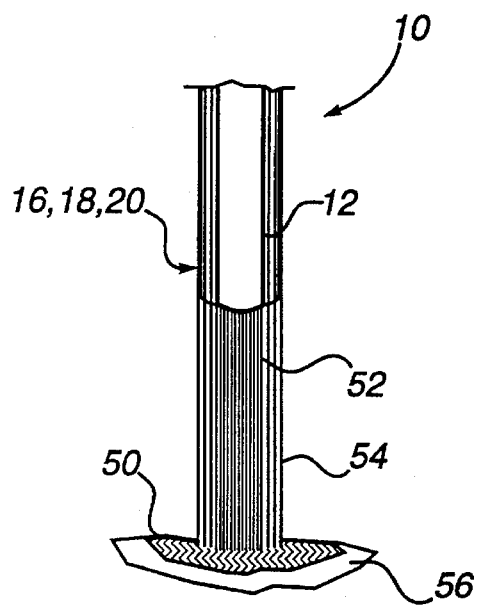
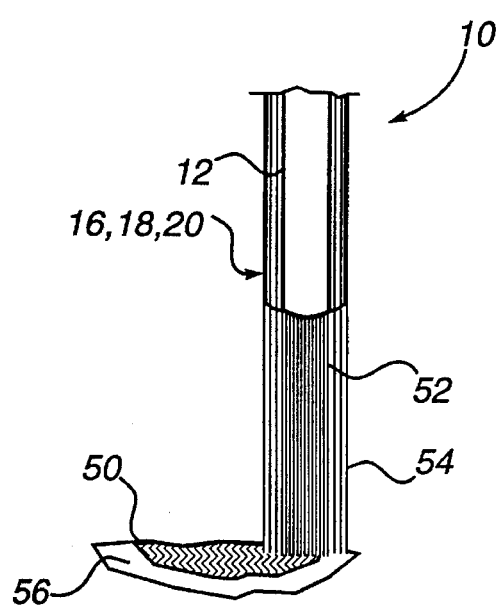
FIG. 6  FIG. 7
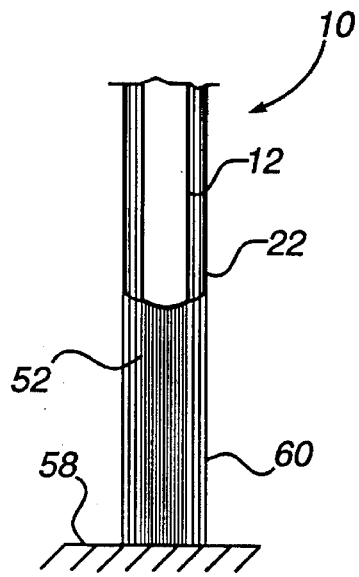
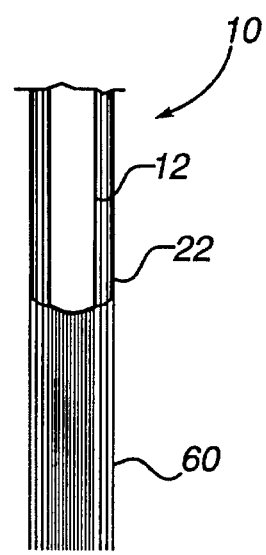
FIG. 8  FIG. 9

BOUNDARY AND PROXIMITY SENSOR APPARATUS FOR A LASER

FIELD OF THE INVENTION

The present invention relates generally to laser apparatus and, more particularly, to a laser having treatment area boundary and proximity sensing capability.

BACKGROUND OF THE INVENTION

Lasers, as is known, are well established as effective means for performing precise operations in myriad surgical and industrial applications. Various forms of surgical lasers, for example, may be found in U.S. Pat. Nos. 3,710,798, 3,865,114, 4,122,853, 4,420,431, 4,644,948, 4,911,711, 4,950,268 and 4,994,058.

In treating topical dermatological lesions such as port wine stains, warts, tumors, and the like, on a patient's skin, a physician commonly employs a surgical laser to alleviate or, preferably, remove the lesions. In practice, the physician must move the activated laser over the area of the lesion while exercising great care not to irradiate the surrounding skin, a process that is both time consuming and painstaking. As a consequence, a typical lesion is, at present, normally treated only once or twice at high power, resulting in conditions under which the lesion frequently does not favorably respond.

Attempts to reduce the time and effort required to perform surgical laser treatment of skin lesions have been proposed. One such system involves a computer, video equipment and a laser-carrying robotic arm. In this system, video images of the lesion boundary are processed by the computer which in turn controls the movement of the robotic arm. When the computer, via the processed video images, detects a boundary of the lesion, the computer sends signals to redirect the movement of the robotic arm such that the laser maintains radiation application within the confines of the area of the lesion. Due to its complex design and construction, however, this system is costly and its usage is presently limited essentially to experimental treatments. Further, with such a system, the physician does not directly control the laser. As a consequence, should one or more of the sophisticated components of the system malfunction during the treatment, the skin surrounding the lesion may become unintentionally radiated and/or the lesion over-radiated. Hence, concentration and attention to the condition of not only the patient but also the functionality of the treatment equipment must be strictly maintained throughout the treatment process.

U.S. Pat. No. 4,122,853 teaches of a laser for use in surgical procedures designed to treat affected tissue without irradiating healthy tissue. Specifically, there is described an infrared laser photocautery device that contains an infrared transparent window in its tip which permits the tip to be brought into contact with biological tissue to be cauterized while excluding surrounding tissue from the effects of the beam. If skillfully manipulated, such a device may reduce inadvertent radiation of healthy tissue. However, as with related laser treatments, the physician must at all times exercise extreme caution not to permit the laser energy from crossing the lesion boundary.

A further problem attendant to laser surgical treatment is the potential for unintentional release of laser radiation into the operation room, such as, for example, when the laser is dropped or accidentally turned away from the target area. U.S. Pat. No. 4,950,268 describes a system for deactivating a surgical laser when laser light is aimed in a direction other than toward the surgical area. However, this system operates by way of a photosensor which is disposed adjacent to the laser housing and which is directed obliquely toward a wall or ceiling surface in the room in which the laser is being used. Should the photosensor detect stray reflected laser radiation in the operation room, the laser is deactivated by control circuitry. Although such a system may be generally effective, a serious disadvantage thereof is manifest, i.e., if the laser were to somehow become misdirected from the surgical area and some object blocked the inadvertently misguided laser radiation from reaching, in at least detectable levels, the room area at which the photosensor is directed, the laser would remain activated and continue to release the potentially damaging laser radiation into the operating room.

An advantage exists, therefore, for any laser, including, but not limited to, a surgical laser, an industrial laser, and the like, having sensing and control systems for automatically and reliably deactivating the laser when the laser radiation is directed at an area not intended to be treated by the laser and when the laser is inadvertently misdirected from a target area.

SUMMARY OF THE INVENTION

The present invention provides a surgical laser capable of automatically turning on and off as the laser passes across the boundary of a biological tissue area under treatment, e.g., a skin lesion. Benefits enjoyed by a laser having the presently disclosed operational characteristics included material reductions in time and effort required by a physician to safely radiate the entirety of lesion per laser application. The quality of treatment of the lesion is thereby enhanced since dermatological lesions typically respond more favorably to numerous treatments at relatively low power than one or two treatments at comparatively high power. Further, accidental irradiation of biological treatment surrounding the affected area is effectively prevented.

Generally, the present invention provides a physician manipulable laser handpiece which carries, in addition to a surgical laser, reflected radiation intensify sensors for detecting the boundary of the affected area being treated (boundary sensors) and proximity sensors for preventing unintended release of laser energy into the operating room.

The boundary sensors desirably work in conjunction with a template of predetermined color, preferably white, circumscribing the lesion's edge, whereby the physician may simply move the laser relatively quickly and freely back and forth over the surgical area without being encumbered by manually activating and deactivating the laser in the boundary regions of the lesion and without fear of accidentally irradiating healthy biological tissue surrounding the lesion. That is to say, the sensors operate, through appropriate control circuitry, to automatically activate the laser while it is situated over the relatively dark colored lesion tissue and automatically deactivate the laser as it passes over the lesion boundary and onto the template.

More specifically, according to the invention, the edge of a skin lesion can be easily detected by the laser handpiece by surrounding the lesion with a substantially white boundary and sensing the light/dark ratio between the lesion and the boundary. This boundary, which serves essentially as a template, can be made of adhesive tape, construction paper or any suitable easily shaped material that is preferably white in color for optimum contrast with the dark colored lesion. The principal on which the present invention operates is termed diffuse reflection. This approach relies upon the amount of light reflected from a surface which reflects light in all directions. The instant invention exploits the difference between the light reflected from a preferably white surface and the relatively dark lesion to ascertain when to activate and deactivate a surgical laser.

The laser handpiece is preferably fitted with three sets of fiber optic cables connected to three separate boundary sensors. Each boundary sensor desirably has an isolated power supply and acts autonomously of the others to turn the laser on and off, thereby insuring fail-safe operation in general accordance with U.S. Navy equipment reliability standards which require a primary system to be backed up by two independent secondary systems. Such fail-safe operation virtually assures that the laser will positively deactivate when it encounters a lesion edge. To still further insure reliable operation, the present laser system preferably also has a conventional foot pedal control, whereby the physician can manually control the laser, if such becomes desired or necessary.

The preferred sensors employed in the instant invention are phototransistors. These sensors produce a current proportional to the amount of reflected light they detect emanating from a surface. In a typical dermatological surgical operation, as the laser moves from the dark lesion to the light boundary, the amount of reflected light dramatically increases, causing an increase in the current flow through the sensor. The greater the difference or light/dark ratio between the light boundary and dark lesion, the better the system operates, hence the provision of the substantially white boundary. The light/dark ratio can be used as a threshold value to turn an optocoupler on and off which, in turn, controls the laser. An advantage of phototransistors as sensors is their ability to be tuned to specific frequencies of light, thereby enabling the sensors to operate without interference from other light sources such as the operating room lights and the laser.

Interfacing the boundary sensors to the laser handpiece advantageously involves the use of fiber optic cables. These cables are positioned around the laser in three concentric circles. Each circle of fiber optic cables connects to one sensor, i.e., using multiplexing apparatus, a number of fiber optic cables can be connected to a single sensor. Further, each sensor preferably includes emitter means and detector means. Thus, alternate cables of each circle can be arranged to serve as emitter and detector cables, respectively. Because all sensors are of all circles are preferably tuned to the same response frequency, one sensor from one circle of fiber optic cables can detect light from another sensor of a different circle, thereby increasing the reliability of the system. Each sensor responds to light reflected directly into the end of a detector fiber optic cable in communication with its detector means. When the sensor detects a significant amount of reflected light, the laser handpiece will be substantially directly over the lesion's boundary, thus causing immediate deactivation of the laser.

As noted hereinabove, in addition to the boundary sensors the instant invention is further preferably provided with proximity sensors. The proximity sensors afford the present invention the additional advantage of operating to deactivate the laser if no solid surface exists within about 6 to about 12 inches from the radiating tip of the laser handpiece. Thus, should the surgeon drop or turn the laser handpiece from the target area and the proximity sensor does not detect a nearby solid surface, the sensor operates to immediately deactivate the laser, thereby preventing stray laser radiation from being emitted into the operating room.

Both the boundary sensors and the proximity sensors are adaptable for use in new lasers as well as in retrofitting of virtually all existing lasers. That is, by virtue of the present invention, it will be possible to equip any type of laser, surgical or otherwise, with sensors which insure that the laser is deactivated when it comes upon an area not intended to be irradiated or when the laser beam does not encounter an object in its relatively immediate vicinity.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein:

FIGS. 6 and 7 illustrate the operation of the boundary sensors carried by the laser handpiece of the present invention;

FIGS. 8 and 9 illustrate the operation of the proximity sensor carried by the laser handpiece of the present invention;

DETAILED DESCRIPTION OF THE INVENTION

Figure 1:
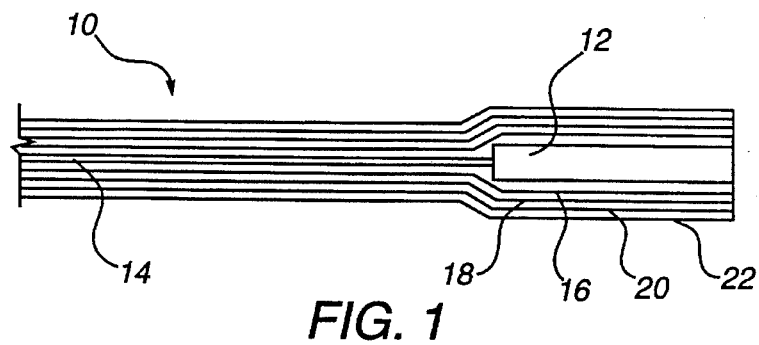
FIG. 1 is a side view, in partial section, of a preferred embodiment of a laser handpiece constructed in accordance with the present invention.
Figure 2:
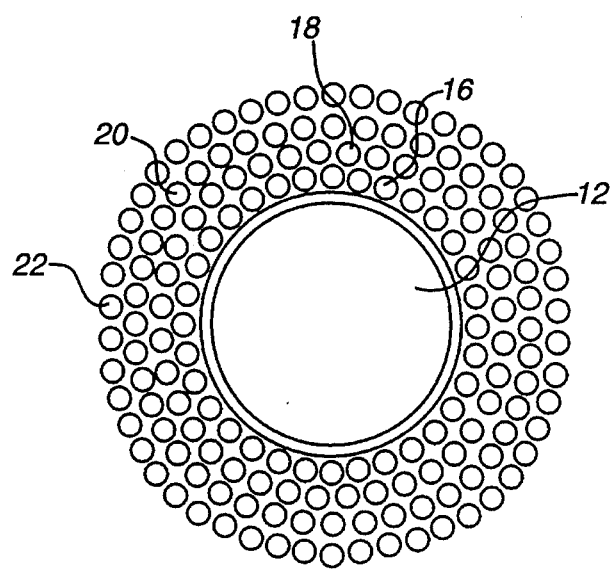
FIG. 2 is an enlarged end view of the laser handpiece illustrated in FIG. 1.

Referring to FIGS. 1 and 2, there is shown a preferred embodiment of the laser handpiece used in the laser system of the present invention. The handpiece, herein generally designated by reference numeral 10, comprises a laser radiation generating and emitting device or laser 12 having joined thereto a power cord 14 that is electrically connected to an unillustrated electrical power supply, the laser 12 being preferably surrounded by a plurality of concentric rings of fiber optic cables 16, 18 and 20 whose functions include transmission of light to and from boundary sensor means to be described hereinafter which transduce the reflected light into an electrical signal that is transmitted to circuitry for controlling operation of the laser 12. Also illustrated is a ring of fiber optic cables 22 that are situated concentrically of laser 12 and which are capable of transmitting light to and from a later-described proximity sensor means, which means also transduces the reflected light into an electrical signal for controlling operation of the laser.

For each ring of fiber optic cables 16, 18, 20 and 22, preferably half the cables emit light and half sense or detect reflected light from a surface at which the radiation emitting tip of the handpiece 10 is directed. As will be later described, if no surface exists within a specified distance from the tip of the handpiece 10, a proximity sensor connected to cables 22 operates through appropriate circuitry to automatically deactivate the laser 12. Moreover, for optimum sensitivity, it is desirable that the light emitting and light detecting cables be substantially uniformly distributed in each cable ring. Consequently, it is preferred that each cable ring 16, 18, 20 and 22 be comprised of alternating light emitting and light detecting cables, as is exemplified by light emitting cables 16A and light detecting cables 16B of ring 16 in FIG. 3. As will be appreciated, the wavelength of light to which the boundary sensor means and proximity sensor means are attuned is discretionary, so long as it does not substantially interfere with the radiation frequency of either the laser or the ambient operating room light. As an example, the sensor means may suitably tuned or predisposed to emit and detect, inter alia, infrared light.

Although a plurality of, specifically three, concentric rings of boundary sensor cables are shown in the drawing figures, it will be appreciated that as few as one ring of such cables, e.g., ring 16, would be substantially sufficient to achieve the boundary sensing capability contemplated by the present invention. However, it is preferred that at least a second ring of boundary cables (ring 18) and, even more desirably, that a third such ring (ring 20) be provided, whereby detection of a boundary of a predetermined surface irregularity to be treated by laser 12, e.g., a dermatological lesion, may be virtually assured. Such three-tiered redundancy (which is generally in accordance with U.S. Navy equipment reliability guidelines) provides for essentially fail-safe operation of the associated laser control circuitry to be described hereinbelow for activating and deactivating the laser 12.

Figure 4:
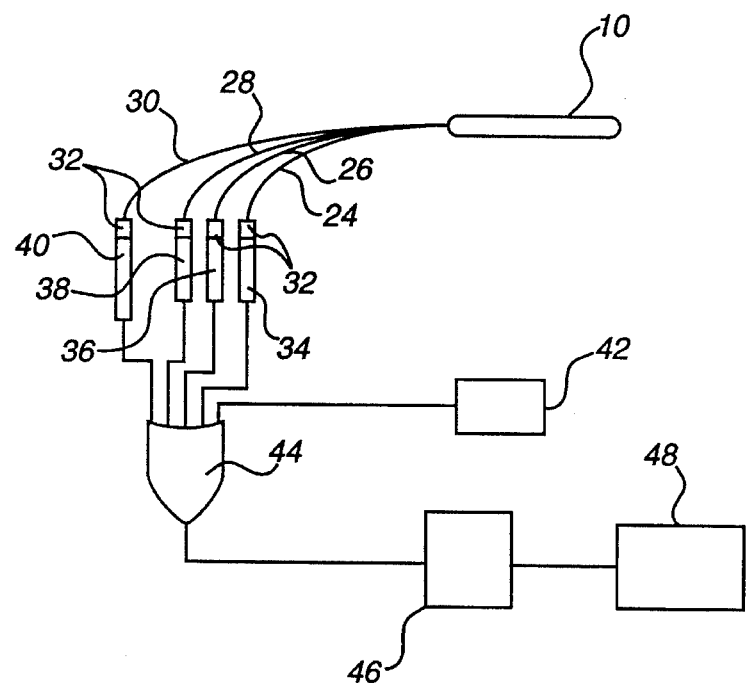
FIG. 4 is a schematic representation of a preferred laser system according to the present invention.

FIG. 4 reveals a schematic representation of a preferred embodiment of a laser system in accordance with the present invention. The system includes the laser handpiece 10 from which extend a plurality of transmission cables, in this instance four, identified by reference numerals 24, 26, 28 and 30 which respectively contain bundles of fiber optic cables that form the rings 16, 18, 20 and 22 surrounding the laser 12. Multiplexor means 32 are provided to convey information transmitted by the light emitting and light detecting cables of each cable ring 16, 18, 20 and 22 to and from various sensor means. Multiplexor means 32 interface the cables 24, 26 and 28 with boundary sensor means 34, 36, 38, respectively, while also interfacing cable 30 with proximity sensor means 40. A conventional foot pedal or related manual switching means 42 is also provided which is connected, along with boundary sensor means 34, 36, 38 and proximity sensor means 40, to an OR gate 44. The OR gate, in turn, through a first optocoupler 46 and a second optocoupler 48 is connected to unillustrated laser "on/off" controls for activating and deactivating the laser 12. Optocouplers 46 and 48 are conventional electronic components which are included in the present system primarily for two purposes. First, they shield the electronics from large transient currents when high voltages are switched on and off. Second, they permit a relatively low voltage switch to turn a very high voltage on and off. Thus, in the instant invention, the optocouplers 46 and 48 enable the relatively low-powered OR gate 44 (5 V, 10 mA, DC) to activate and deactivate the laser (110 V AC).

Each of the boundary sensor means 34, 36, 38 is configured to output a digital zero (0) signal to the OR gate 44 when it detects a predetermined threshold level of reflected light from a surface. Whereas, the proximity sensor means 40 is configured to output a digital zero (0) signal should no reflected be detected, i.e., when there is no substantially solid surface detected within a predetermined distance from the radiation emitting tip of the laser handpiece. Further, the manual switching means 42 transmits a digital zero (0) signal when the laser is manually deactivated thereby. Therefore, in any instance wherein the OR gate 44 receives at least one digital zero (0) signal, the laser 12 becomes deactivated. Hence, activation of the laser can only occur when the OR gate 44 receives all digital one (1) signals from sensors 34, 36, 38, 40 and manual switching means 42. TABLE 1 graphically depicts the possible conditions of the signals transmitted to the OR gate 44 in a laser system constructed in accordance with the presently preferred embodiment of the present invention, i.e., a system including boundary sensor means 34, 36, 38, proximity sensor means 40 and manual switching means 42.

TABLE 1

| Boundary Sensor #34 | Boundary Sensor #36 | Boundary Sensor #38 | Proximity Sensor #40 | Manual Switch #42 | Laser Status |
| --- | --- | --- | --- | --- | --- |
| 1 | 1 | 1 | 1 | 1 | 1* |
| 0 | 1 | 1 | 1 | 1 | 0 |
| 1 | 0 | 1 | 1 | 1 | 0 |
| 0 | 0 | 1 | 1 | 1 | 0 |
| 1 | 1 | 0 | 1 | 1 | 0 |
| 0 | 1 | 0 | 1 | 1 | 0 |
| 1 | 0 | 0 | 1 | 1 | 0 |
| 0 | 0 | 0 | 1 | 1 | 0 |
| 1 | 1 | 1 | 0 | 1 | 0 |
| 0 | 1 | 1 | 0 | 1 | 0 |
| 1 | 0 | 1 | 0 | 1 | 0 |
| 0 | 0 | 1 | 0 | 1 | 0 |
| 1 | 1 | 0 | 0 | 1 | 0 |
| 0 | 1 | 0 | 0 | 1 | 0 |
| 1 | 0 | 0 | 0 | 1 | 0 |
| 0 | 0 | 0 | 0 | 1 | 0 |
| 1 | 1 | 1 | 1 | 0 | 0 |
| 0 | 1 | 1 | 1 | 0 | 0 |
| 1 | 0 | 1 | 1 | 0 | 0 |
| 0 | 0 | 1 | 1 | 0 | 0 |
| 1 | 1 | 0 | 1 | 0 | 0 |
| 0 | 1 | 0 | 1 | 0 | 0 |
| 1 | 0 | 0 | 1 | 0 | 0 |
| 0 | 0 | 0 | 1 | 0 | 0 |
| 1 | 1 | 1 | 0 | 0 | 0 |
| 0 | 1 | 1 | 0 | 0 | 0 |
| 1 | 0 | 1 | 0 | 0 | 0 |
| 0 | 0 | 1 | 0 | 0 | 0 |
| 1 | 1 | 0 | 0 | 0 | 0 |
| 0 | 1 | 0 | 0 | 0 | 0 |
| 1 | 0 | 0 | 0 | 0 | 0 |
| 0 | 0 | 0 | 0 | 0 | 0 |

*Operational mode (laser activated)

Figure 3:
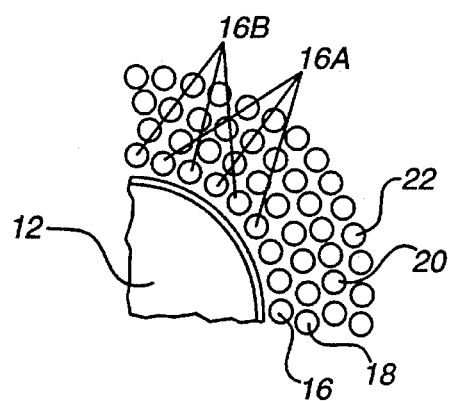
FIG. 3 is a fragmentary and further enlarged end view of the laser handpiece shown in FIG. 1.
Figure 5:
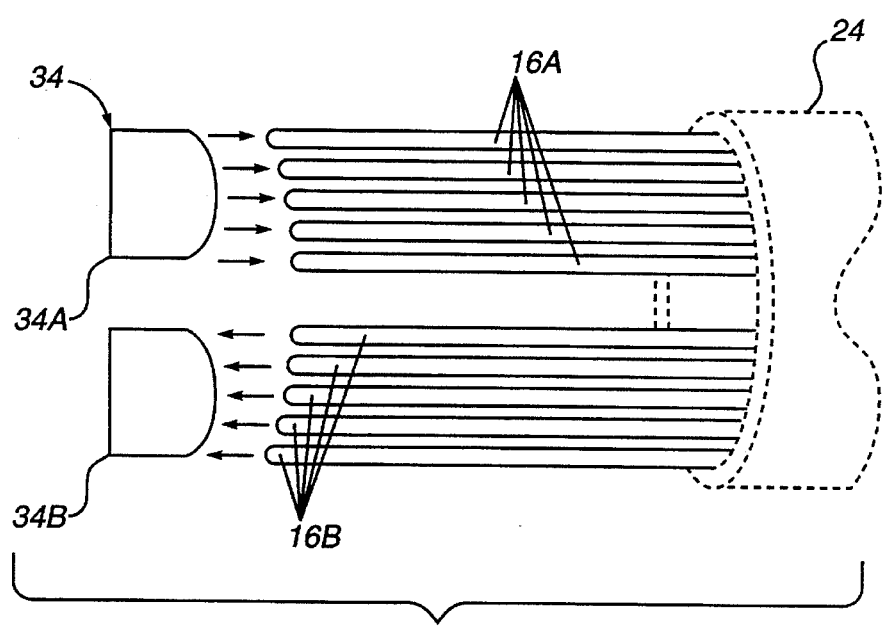
FIG. 5 is a magnified view of a multiplexor adapted for use in the laser system shown in FIG. 4.

Multiplexor means 32 functions, as mentioned hereinabove, to interface transmission cables 24, 26, 28 and 30 containing bundles of fiber optic cables, including both light emitting and light detecting species, with boundary sensors 34, 36, 38 and proximity sensor 40. FIG. 5 schematically reveals on a greatly magnified scale the operation of the multiplexor means 32, by way of specific reference to the interaction between boundary sensor 34 and light emitting fiber optic cables 16A and light detecting fiber optic cables 16B of fiber optic cable ring 16 (FIGS. 1–3). It will be appreciated that the following description will serve, by way of reference, as description of the operations occurring at the remaining stations of the multiplexor means 32, i.e., at sensor means 36, 38 and 40.

Each sensor means, either boundary sensor means 34, 36 or 38, or proximity sensor means 40, is comprised of an emitting element and a detecting element. In the present example illustrated in FIG. 5, wherein the multiplexor means 32 is omitted for clarity of illustration, boundary sensor means 34 is seen to include an emitting element 34A from which radiation is emitted and thereafter transmitted by fiber optic cables 16A to be radiated onto a selected target surface, such as, for example, a surgical treatment area. Likewise, the boundary sensor means 34 further includes a detecting element 34B which receives radiation that is reflected from the target area and transmitted therefrom by the fiber optic cables 16B. As a specific example, if, for instance, infrared light emitted from emitting element 34A were projected into the ends of the fiber optic cables 16A, that light would be transmitted along those cables and emitted from the opposite ends thereof at laser handpiece 10. Concurrently, infrared light which may be reflected from the target area into the ends of the fiber optic cables 16B at the laser handpiece will be transmitted along cables 16B and projected into detecting element 34B. Should the detected light exceed a threshold intensity level, the boundary sensor 34 transmits a deactivation signal to OR gate 44 and the laser 12 will be automatically deactivated.

Appreciation of a preferred application of the laser system of the present invention will be had with reference to FIGS. 6 and 7. In general, these figures illustrate the operation of the boundary sensor means and, in particular, their operation in a dermatological laser treatment. Looking first to FIG. 6, the laser handpiece 10 is shown in an instant in time at which it is located over a relatively dark colored skin lesion 50. In such a position, the laser light 52 and the radiation 54 from the boundary sensor means impinges upon the lesion 50. However, when located over the lesion the light emitted from the boundary sensor means 34, 36, 38 does not reflect from the relatively dark colored lesion with sufficient intensity to trigger the boundary sensor means to transmit a signal to the OR gate 44 (FIG. 4) to deactivate the laser 12.

Turning to FIG. 7, wherein the laser handpiece 10 is shown at a different instant in time whereat a fraction of the light from the laser and the boundary sensor means is caused to impinge upon a light-colored, preferably substantially white, boundary 56. Boundary 56 is essentially a template means which is appropriately placed so as to closely circumscribe the lesion's edge and may be formed of adhesive tape, construction paper, putty or any suitable light-colored and easily shaped material. Because of its color, the boundary 56 reflects the light from boundary sensor means 34, 36, 38 with sufficient intensity, i.e., at or above a predetermined threshold, whereby one or more of the boundary sensor means are caused to transmit a laser deactivation signal to the OR gate 44 so as to shut off the laser within 1/1000 of a second after passage of the laser beyond the boundary of the lesion.

FIGS. 8 and 9 depict the operation of the proximity sensor means 40 whose function it is to deactivate the laser 12 in the event the radiation 58 emitted from the proximity sensor means fails to contact a surface within a predetermined distance from the laser handpiece 10, e.g., within about 6 to 12 inches from the handpiece and, normally, about 6 to 8 inches therefrom. This feature serves to prevent the laser light from accidentally being released into the operating room and can be used in any surgical or industrial procedure requiring the use of a laser.

FIG. 8 in particular shows the laser handpiece 10 situated over a surface 58, which may include, inter alia, a target area for surgical treatment by laser 12. Radiation 60 (e.g., infrared light) emitted from the emitting element of the proximity sensor means 40 is reflected from surface 58 and is detected by the detecting element of the proximity sensor means. Preferably, and unlike the boundary sensor means which require a certain threshold of light to be detected in order to deactivate the laser 12, the proximity sensor means leaves the laser light 52 on when any reflected light from the proximity sensor means is detected. As can be seen in FIG. 9, in the absence of a surface proximate the tip of the laser handpiece, no light from the radiation emitting fiber optic cables associated with the proximity sensor means can be reflected back into the radiation detecting fiber optic cables thereof. Hence, under such conditions, the proximity sensor means 40 immediately sends a signal to deactivate the laser.

Figure 10:
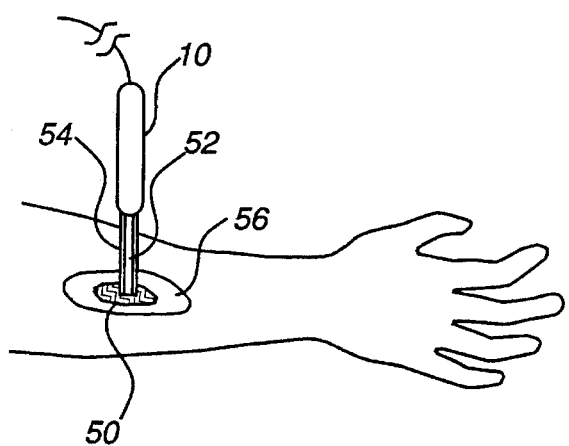
FIGS. 10 and 11 are views similar to FIGS. 6 and 7 and represent the process by which the present invention may be used to remove a lesion from a patient's arm.
Figure 11:
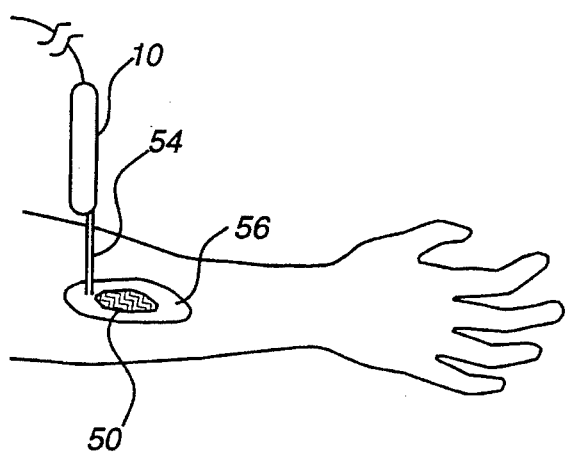

In FIGS. 10 and 11, the present invention is depicted as it would be employed in removal of skin lesions on a patient's arm. In FIG. 10, the laser handpiece 10 is positioned over the relatively dark lesion 50. Because the quantity of light reflected from the lesion's surface satisfies the minimal requirements of the proximity sensor means but is insufficient to trigger to the boundary sensor means, the laser 12 remains activated. In FIG. 11, the laser handpiece has been moved over the light colored boundary 56. The increase in intensity of reflected light from the treatment surface has been detected by the boundary sensor(s) and the laser light 52 has been shut off.

Figure 12:
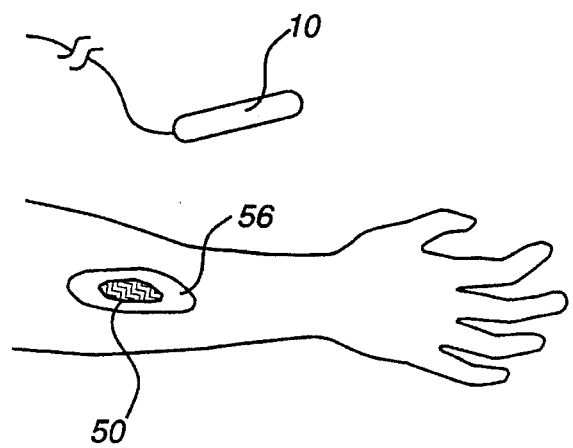
FIG. 12 is a view depicting the automatic deactivation of the laser at such time when the laser is directed away from the target surgical area.

FIG. 12 shows a situation, e.g., an accident in the operating room, where the laser handpiece 10 has been inadvertently turned on its side and the proximity sensor has immediately deactivated the laser, thereby assuring that the laser light does not become accidently released into the operating room. As in the situation shown in FIG. 9, no light has been reflected back into the proximity sensor means fiber optic detecting cables, thus the proximity sensor means has turned off the laser. Although not illustrated, it will be understood that additional proximity sensor means may be provided to supplement the single proximity sensor means herein disclosed in order to achieve in the proximity sensing system of the present invention a degree of fail-safe operation comparable to that of the boundary sensor means.

Moreover, notwithstanding their preferred usage with topical surgical lasers it is contemplated that, within the scope of the present invention, any laser apparatus, including, but not limited to, surgical and industrial laser devices, may benefit from adaptation thereto of the boundary sensing and/or proximity sensing systems as disclosed herein.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A laser system comprising:

a laser which is operable to emit laser radiation and adapted to be grasped by a user and freely passed over a treatment area;

control means operatively connected to said laser for activating and deactivating said laser; and means for sensing a boundary of said treatment area, said means for sensing a boundary being operable to transmit a signal to said control means to deactivate said laser upon passage of laser radiation emitted by said laser beyond a boundary of said treatment area and to transmit a signal to said control means to activate said laser upon passage of laser radiation emitted by said laser within said boundary.

2. The system of claim 1 wherein said sensing means transmit said signal to said control means to deactivate said laser when reflected radiation from beyond said boundary exceeds a predetermined threshold.

3. The system of claim 1 wherein said sensing means include at least one boundary sensor including means for emitting radiation and means for detecting radiation emitted by said emitting means and reflected from said treatment area.

4. The system of claim 3 further comprising a first plurality of fiber optic cables disposed about and extending along said laser, said first plurality of fiber optic cables being positioned to receive radiation from said emitting means and to transmit said radiation to said treatment area.

5. The system of claim 4 further comprising a second plurality of fiber optic cables disposed about and extending along said laser, said second plurality of fiber optic cables being positioned to receive reflected radiation from said treatment area and to transmit said reflected radiation to said detecting means.

6. The system of claim 5 further comprising multiplexor means for enabling communication of said first and second pluralities of fiber optic cables with said at least one boundary sensor.

7. The system of claim 6 wherein said first and second pluralities of fiber optic cables in communication with each said at least one boundary sensor are disposed substantially uniformly about said laser.

8. The system of claim 7 wherein, for each said at least one boundary sensor, said first and second pluralities of fiber optic cables in communication therewith are disposed together substantially in a ring about said laser.

9. The system of claim 8 wherein, for each said ring, fiber optic cables of said first plurality of fiber optic cables alternate with fiber optic cables of said second plurality of fiber optic cables.

10. The system of claim 9 wherein said sensing means include a plurality of said boundary sensors, each of said plurality of boundary sensors forming about said laser a separate concentric ring formed of said first and second pluralities of fiber optic cables.

11. The system of claim 10 wherein said sensing means include three of said boundary sensors.

12. The system of claim 10 further comprising proximity sensor means for transmitting a signal to said control means to deactivate said laser should said proximity sensor means fail to sense a substantially solid surface within a predetermined distance therefrom and for transmitting a signal to said control means to activate said laser should said proximity sensor means sense said surface.

13. The system of claim 3 wherein said sensing means include a plurality of said boundary sensors.

14. The system of claim 13 wherein said sensing means include three of said boundary sensors.

15. The system of claim 1 further comprising a template adopted for circumscribing said treatment area, said template being lighter in color than said treatment area in order to enhance reflection of radiation from beyond said boundary.

16. The system of claim 15 wherein said template is formed of substantially white material.

17. The system of claim 1 further comprising means for manually transmitting laser activation and deactivation signals to said control means.

18. A laser system comprising:
a laser which is operable to emit laser radiation and adapted to be grasped by a user and freely passed over a treatment area;
control means operatively connected to said laser for activating and deactivating said laser; and
proximity sensor means for transmitting a signal to said control means to deactivate said laser should said proximity sensor means fail to sense a substantially solid surface within a predetermined distance therefrom and for transmitting a signal to said control means to activate said laser should said proximity sensor means sense said surface.

19. The system of claim 18 wherein said proximity sensor means includes means for emitting radiation and means for detecting radiation emitted by said emitting means and reflected by said surface.

20. The system of claim 19 further comprising a first plurality of fiber optic cables disposed about and extending along said laser, said first plurality of fiber optic cables being positioned to receive reflected radiation from said surface and to transmit said reflected radiation to said detecting means.

21. The system of claim 20 further comprising a second plurality of fiber optic cables disposed about and extending along said laser, said second plurality of fiber optic cables being positioned to receive reflected radiation from said surface and to transmit said reflected radiation to said detecting means.

22. The system of claim 21 further comprising multiplexor means for enabling communication of said first and second pluralities of fiber optic cables with said proximity sensor means.

23. The system of claim 22 wherein said first and second pluralities of fiber optic cables are disposed substantially uniformly about said laser.

24. The system of claim 23 wherein said first and second pluralities of fiber optic cables are disposed substantially in a ring about said laser.

25. The system of claim 24 wherein fiber optic cables of said first plurality of fiber optic cables alternate with fiber optic cables of said second plurality of fiber optic cables in said ring.

26. A laser system comprising:
a laser which is operable to emit laser radiation and adapted to be grasped by a user and freely passed over a treatment area;
control means operatively connected to said laser for activating and deactivating said laser;
boundary sensor means for sensing a boundary of said treatment area, said means for sensing a boundary being operable to transmit a signal to said control means to deactivate said laser upon passage of laser radiation emitted by said laser beyond a boundary of said treatment area and to transmit a signal to said control means to activate said laser upon passage of laser radiation emitted by said laser within said boundary; and
proximity sensor means for transmitting a signal to said control means to deactivate said laser should said proximity sensor means fail to sense a substantially solid surface within a predetermined distance therefrom and for transmitting a signal to said control means to activate said laser should said proximity sensor means sense said surface.

27. The system of claim 26 wherein said boundary sensor means and said proximity sensor means each include means for emitting radiation and means for detecting radiation emitted by said emitting means and reflected by at least one of said treatment area and said surface.

28. The system of claim 27 further comprising, for each of said boundary sensor means and proximity sensor means, a first plurality of fiber optic cables disposed about and extending along said laser, said first plurality of fiber optic cables being positioned to receive radiation from said emitting means and to transmit said radiation to said at least one of said treatment area and said surface.

29. The system of claim 28 further comprising, for each of said boundary sensor means and proximity sensor means, a second plurality of fiber optic cables disposed about and extending along said laser, said second plurality of fiber optic cables being positioned to receive reflected radiation from at least one of said treatment area and said surface and to transmit said reflected radiation to said detecting means.

30. The system of claim 29 further comprising multiplexor means for enabling communication of said first and second pluralities of fiber optic cables with said means for sensing a boundary and said proximity sensor means.

31. The system of claim 30 wherein, for each of said boundary sensor means and proximity sensor means, said first and second pluralities of fiber optic cables in communication therewith are disposed together substantially uniformly about said laser.

32. The system of claim 31 wherein, for each of said boundary sensor means and proximity sensor means, said first and second pluralities of fiber optic cables in communication therewith are disposed together substantially in a ring about said laser.

33. The system of claim 32 wherein, for each said ring, fiber optic cables of said first plurality of fiber optic cables alternate with fiber optic cables of said second plurality of fiber optic cables.

34. The system of claim 26 further comprise a template adapted for circumscribing said treatment area, said template being lighter in color than said treatment area in order to enhance reflection of radiation from beyond said boundary.

35. The system of claim 34 wherein said template is formed of substantially white material.

36. The system of claim 26 further comprising means for manually transmitting laser activation and deactivation signals to said control means.

* * * * *